(12) United States Patent
Cui

(10) Patent No.: US 8,092,793 B2
(45) Date of Patent: Jan. 10, 2012

(54) TREATING INFLAMMATORY BOWEL DISEASE WITH LIVE BACTERIA

(75) Inventor: Yunlong Cui, Jiaonan (CN)

(73) Assignee: Qingdao East Sea Pharmaceuticals, Ltd., Shandong Province (CN)

( * ) Notice: Subject to any disclaimer, the term of this patent is extended or adjusted under 35 U.S.C. 154(b) by 972 days.

(21) Appl. No.: 11/763,094

(22) Filed: Jun. 14, 2007

(65) Prior Publication Data

US 2008/0003207 A1 Jan. 3, 2008

Related U.S. Application Data

(63) Continuation-in-part of application No. 11/191,712, filed on Jul. 28, 2005, now abandoned.

(30) Foreign Application Priority Data

Dec. 15, 2004 (CN) .......................... 2004 1 0098660
Jan. 29, 2007 (CN) .......................... 2007 1 0002692

(51) Int. Cl.
*A61K 35/74* (2006.01)
*A01N 63/00* (2006.01)
*A61P 1/00* (2006.01)

(52) U.S. Cl. .................................. 424/93.41; 424/93.46
(58) Field of Classification Search .................. None
See application file for complete search history.

(56) References Cited

U.S. PATENT DOCUMENTS

| 6,723,326 | B1 | 4/2004 | Farmer |
| 2004/0028689 | A1* | 2/2004 | Borody ........................ 424/184.1 |
| 2005/0100535 | A1 | 5/2005 | Farmer et al. |
| 2006/0127381 | A1 | 6/2006 | Cui |
| 2008/0118482 | A1 | 5/2008 | Cui |
| 2008/0199444 | A1 | 8/2008 | Cui |

FOREIGN PATENT DOCUMENTS

| EP | 1 022 023 | 10/2005 |
| WO | WO00/61201 | 10/2000 |
| WO | WO01/34168 | 5/2001 |

OTHER PUBLICATIONS

Wang et al, "Tai Ning bovine protein induced colonic mucosal immune treatment of ulcerative colitis", 2000, downloaded from http://www.chemyq.com/health/ep6/55784_93A9A.htm, 2005, pp. 1-2.*
Wan et al., "Effect of *Bacillus coagulans* tablets on the treatment of experimental diarrhea in mice,"Chinese J. Microecology 17(6):415-418 (2005), English abstract.
Wang et al., "The effects of *Bacillus coagulans* on immune functions, amine content of feces and ammonia content of intestinal tract in mice," Chinese J. Microecology 18(1):6-8(2006), English abstract.
Gregor Reid; "Probiotics in the Treatment of Diarrheal diseases"; Current Infectious Disease Reports; vol. 2, pp. 78-83; 2000.

* cited by examiner

*Primary Examiner* — Laura Schuberg
(74) *Attorney, Agent, or Firm* — Occhiuti Rohlicek & Tsao LLP

(57) ABSTRACT

This invention relates to using live beneficial bacteria for treating inflammatory bowel disease, such as ulcerative colitis and Crohn's disease.

14 Claims, No Drawings

TREATING INFLAMMATORY BOWEL DISEASE WITH LIVE BACTERIA

CROSS-REFERENCE TO RELATED APPLICATIONS

This application is a continuation-in-part application of U.S. patent application Ser. No. 11/191,712, filed Jul. 28, 2005, which claims priority from Chinese Patent Application No. 200410098660.4, filed Dec. 15, 2004. This application also claims priority from Chinese Patent Application No. 200710002692.3, filed Jan. 29, 2007. The contents of these related applications are incorporated herein by reference in their entireties.

BACKGROUND

Inflammatory bowel disease (IBD) is a chronic disorder of the gastrointestinal tract characterized by inflammation of the intestines or colon. Symptoms of IBD include abdominal cramping, persistent diarrhea, and colorectal bleeding. The cause for IBD is still elusive. Some evidence suggests that it may be caused by an overactive immune system that attacks various tissues of the gastrointestinal tract.

Ulcerative colitis and Crohn's disease are two main forms of IBD. Although both are disorders causing inflammation of the digestive tract, they differ as to the nature and location of the inflammatory reactions in the guts. Ulcerative colitis is restricted to the colon and the anus and inflammation caused by it only affects mucosa. In contrast, Crohn's disease can affect the whole gastrointestinal tract, i.e., from mouth to anus, although it commonly affects the lower part of the small intestine (ileum). Further, inflammation caused by Crohn's disease extends deep into the bowel wall.

Treatment for IBD, including drugs, nutrition supplements, surgery, or a combination thereof, may help control the disease by inducing or maintaining remission, or by reducing recurrence. They, however, do not cure the disease.

SUMMARY

The present invention is based on the observation that live beneficial bacteria are effective in treating inflammatory bowel diseases.

Accordingly, the invention provides a method for treating an inflammatory bowel disease (e.g., ulcerative colitis or Crohn's disease) with a composition containing an effective amount of a live beneficial bacterium, such as *Bacillus* or *Clostridium*, or a combination of different types of beneficial bacterium. The Bacillus can be *Bacillus coagulans* (e.g., a strain deposited at the Chinese General Microbiological Culture Collection Center, Institute of Microbiology, Chinese Academy of Sciences, Haidian, Beijing 100080, P.O.Box 2714 under the Budapest Treaty and assigned the deposit number CGMCC NO. 1207) or *Bacillus subtilis*. The *Clostridium* can be *Clostridium butyricum* (e.g., a strain deposited at the same depository under the Budapest Treaty and assigned the deposit number CGMCC No. 0313.1). The effective amount of the live bacterium can be ranged from $10^6$ to $10^{12}$ cfu per day.

The composition described herein can be a pharmaceutical composition, which can be administered orally. It can be formulated in a form of tablet, capsule, powder or liquid. The amount of the live bacterium in this composition can be in the range of $1\times10^6$ CFU/g to $1\times10^{12}$ CFU/g.

This composition can also be a food product (e.g., yogurt or milk) or a dietary supplement (supply nutrients or herbal products).

The details of one or more embodiments of the invention are set forth in the description below. Other features, objects, and advantages of the invention will be apparent from the description and drawings, and from the claims.

DETAILED DESCRIPTION

The present invention provides a method of treating IBD (e.g., ulcerative colitis or Crohn's disease) in a patient who needs this treatment with an effective amount of a composition containing a live beneficial bacterium.

The term "effective amount" as used herein, refers to an amount or concentration of an agent utilized for a period of time (including acute or chronic administration and periodic or continuous administration) that is effective within the context of its administration for causing an intended effect or physiological outcome. An effective amount of a live beneficial bacterium for use in this invention include, for example, amounts that are effective for preventing or inhibiting intestinal or colonic inflammation in a subject, or for relieving or ameliorating the symptoms of IBD, e.g., abdomen pain, diarrhea, or colorectal bleeding.

The term "treating IBD" used herein, unless otherwise indicated, means preventing or inhibiting bowel inflammation, relieving the above-described symptoms of IBD, or reversing, ameliorating, or inhibiting the progress of IBD.

The term "beneficial bacterium" refers to any bacterium in the intestine and colon that benefits its host in various ways. A beneficial bacterium can form on the top of the intestinal and colonic walls a protective layer, which blocks harmful bacteria and their toxins from damaging or penetrating the walls. Alternatively or in addition, a beneficial bacterium can secret acidic substances (e.g., short-chain fatty acids) resulting in an acidic environment unsuitable for the growth of harmful bacteria. As a result, beneficial bacteria reduce the level of toxins that are generated by harmful bacteria. Moreover, a beneficial bacterium can generate digestive enzymes to decompose food. It can promote digestion by secreting the above-mentioned short-chain fatty acids, which stimulate intestine and colon movement.

The composition for treating IBD can include one or more types of beneficial bacteria (e.g., *B. coagulans, C. butyricum*, or a combination thereof). The live beneficial bacteria can be prepared by fermentation carried out under various conditions. One type of bacteria can be cultured individually or co-cultured with another type of bacteria. After the fermentation, the bacteria can be collected by centrifugation and the resultant wet pellets can then be dried by a method that preserves the activity of the bacteria. Suitable drying methods include freeze drying, spray drying, heat drying, or a combination thereof.

The bacteria powder thus obtained can be mixed with a pharmaceutically acceptable carrier to form a pharmaceutical composition. "Acceptable" means that the carrier must be compatible with the active ingredient of the composition (and preferably, capable of stabilizing the active ingredient) and not deleterious to the subject to be treated. Suitable carriers include microcrystalline cellulose, mannitol, glucose, defatted milk powder, polyvinylpyrrolidone, and starch, or a combination thereof. This composition can then be presented in a variety of forms, such as tablet, capsule, powder, or liquid. In this composition, the concentration of the live bacteria is in the range of $10^6$ to $10^{12}$ cfu/g. When the composition contains more than one types of bacteria, the different types of bacteria can be in any ratio, as long as the total amount of bacteria is at least $10^6$ cfu/g.

The composition described herein can be administered to a patient via suitable routes, e.g., oral administration, once or multiple times per day or administered once every several days. A solid formulation for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microglycolate, and alginic acid. Tablet binders that can be used include acacia, methylcellulose, sodium carboxymethylcellulose, polyvinylpyrrolidone (Povidone3), hydroxypropyl methylcellulose, sucrose, starch, and ethylcellulose. Lubricants that can be used include magnesium stearates, stearic acid, silicone fluid, talc, waxes, oils, and colloidal silica.

Of note, a solid formulation can be designed such that the active composition is released in the intestines. For example, the active composition is confined in a solid sub-unit or a capsule compartment that has a matrix, a wall or a closure containing an enteric polymer which dissolves or disperses at the pH of the small or large intestines to release the active composition in the intestines. Suitable polymers are described in, e.g., U.S. Pat. No. 5,705,189.

The bacteria powder also can be part of a food product (e.g., yogurt, milk, or soy milk) or a food supplement (e.g., supply nutrients or herbal products). Such food products can be prepared by methods well known in the food industry.

Effective amounts of the live bacterium used in the method described herein can be determined based on factors such as the patient's age, severity and duration of IBD, and other medical conditions. In general, the effective amount ranges from $10^6$ to $10^{12}$ cfu per day.

The composition described herein can be used in manufacturing medicaments for treating IBD.

Not to be bound by theory, live beneficial bacteria may function via the following mechanisms to treat IBD. First, they modulate immune responses by reducing stimulating index of B cells and increasing that of T cells. Second, they reduce the levels of inflammatory factors, such as IL-8 and TNF-α, thus ameliorating local inflammation. Finally, they reduce the levels of IgG, which are shown to be involved in the development of IBD.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

EXAMPLE 1

Preparation of Bacteria Powder Containing Live *Clostridium butyricum*

*Clostridium butyricum* CGMCC No. 0313.1 stored in a tube was suspended in a 100 ml autoclaved Erlenmeyer flask containing 10 ml physiological saline and suitable amount of glass beads. After 10 minutes, 1 ml bacteria solution was inoculated into a 250 ml Erlenmeyer flask filled with 50 ml amplification media containing tryptone (1%), yeast extract (0.3%), beef exact (1%), glucose (0.5%), soluble starch (0.1%), sodium chloride (0.5%), anhydrous sodium acetate (0.3%), and L-cysteine (0.05%). The bacteria were cultured in a shaker at 37° C. and shaken at the speed of 190 rpm for 24 hours. Then the bacteria solution was transferred to a 2500 ml baffled Erlenmeyer flask containing 450 ml amplification media, cultured at 37° C. with shaking for another 24 hours. The bacteria solution was examined under microscope for contamination. If no contamination had occurred, the bacteria solution was transferred into a seeding tank containing 4.5 L amplification media and further cultured under aerobic conditions (air inflation amount 3:1) for yet another 24 hours. The resulting bacteria solution, if not contaminated, was transferred to a fermentation tank filled with fermentation media and cultured under aerobic conditions for 24 hours. When the sporulation rate reached 80% (determined by microscopic examination), the fermentation was terminated. The bacteria were collected by centrifuging at 12,000 rpm. Wet bacteria pellets were collected and weighed. The same amount (by weight) of defatted milk powder was mixed with the bacteria, dried, pulverized and kept at room temperature ready for use.

EXAMPLE 2

Preparation of Live *Clostridium butyricum* Capsule

The following is a formulation of live *Clostridium butyricum* capsule:

| Components | % (Weight) |
| --- | --- |
| Live bacterial powder of *Clostridium butyricum* | 20.00 parts |
| Microcrystalline cellulose | 40.00 parts |
| Glucose | 60.00 parts |

The above-described three components were mixed completely and made into capsules in unit dosage according to conventional encapsulating technology.

EXAMPLE 3

Induction of Inflammatory Bowel Disease in Rats

Calf colonic mucous membrane proteins were prepared as described below. Mucous membranes were scraped from the colons derived from new-born calves. Mucous membrane proteins were then extracted by freezing and thawing the membranes repeatedly. The proteins were purified and concentrated using methods known in the art and then lyophilized and kept at 4° C., ready for use.

The calf colonic mucous membrane proteins thus obtained were mixed with complete Freund's adjuvant at the ration of 1:1 (w/v) to produce complete antigens, which were used to immunize SD rats. The rats (male, 200±20 g) were first injected with 4 mg complete antigens at their feet, then injected with 6 mg complete antigens at days 10, 17, and 24 at their feet, back, groin, and abdomen, and finally injected with membrane proteins only at day 31 at their feet, back, groin, and abdomen.

At day 35, these immunized rats were starved for 24 hours, then anesthetized with Amobarbital Sodium and treated according to the following steps. First, the rats were subjected to enema with 1.5 ml 2%(v/v) formaldehyde for one hour and washed with physiological saline. The rats were then subjected to enema with 2 ml mucous membrane proteins (4 mg/ml) for 2 hours and washed with physiological saline. Three days later, two randomly picked rats were sacrificed and the pathological conditions of their colon walls (e.g., colon wet weight, mucous membrane ulcers and damages, lymphocyte infiltration) were examined following the standards below:

(a) Colon wet weight index=colon wet weight/100 g body weight (b) Mucous membrane ulcers index: the levels of membrane ulcers are determined as follows. Rat colon was cut to open and all contents inside were removed. The upper part and the lower part of the colons were numbered, immobilized on a hard paper plate, and photographed. The colons thus treated were fixed in formaldehyde solutions and the blooding areas (typically linear) were measured. The ulcer level of each blooding area was evaluated according to the standard below based on its length: blooding area<1 mm=1 point; 1-2 mm=2 points; 2-3 mm=3 points; 3-4 mm=4 points. If a blooding area is longer than 4 mm, it would be divided into two or more areas. The points would be doubled if the width of a blooding area is greater than 2 mm. The index of membrane ulcers refers to the sum of the points determined as described above.

(c) Mucous membrane damage index: Rat colons were separated into small pieces, dehydrated with ethanol, fixed with paraffin, sliced (5 μm), stained with hematoxylin and eosin, and subjected to microscopic examination and photograph. The levels of membrane damage were determined as follows:

1 point: membrane surfaces have a small amount of secreted substances; slight blooding, swollen, and/or lymphocytes infiltration found inside the membranes.

2 point: membrane surfaces have a large amount of secreted substances; a small amount of the epithelium came off; the membranes show clear blooding, swollen, and/or lymphocytes infiltration;

3 point: membrane surfaces have a huge amount of secreted substances; a large amount of the epithelium came off; the membranes show clear inflammation and/or ulcers.

The levels of membrane damage of the rectum, the lower part of the colon, and the upper part of the colon of each rat were calculated as described above. The mucous membrane damage index refers the means of membrane damage levels.

(d) Mesentery lymphocytes stimulation index: rat mesentery lymphocytes were isolated, filtrated through a cell sieve, washed twice with sterilized PBS, and centrifuged at 1000 rpm for 5 minutes. Cells thus obtained were suspended in 1640 medium at the concentration of $5\times10^5$/ml, and distributed into a 96-well cell culturing plate (100 μl per well). Each testing well was further added with 100 μl ConA at the final concentration of 3 μg/ml or 100 μl LPS at the final concentration of 5 μg/ml. ConA or LPS was not added to control wells. Cells were cultured at 37° C. with 5% $CO_2$ for 72 hours and then 20 μl MTT (5 mg/ml) were added to each well. After inducing the cells for another 4 hours, the OD value of each well was determined under 540 nm. The lymphocyte stimulate index=OD of stimulated cells (with ConA or LPS)/OD of non-stimulated cells (without ConA or LPS).

(e) IL-8, TNF-α, and IgG: blood samples from sacrificed rats were obtained and kept at 4° C. overnight and centrifuged at 3000 rpm for 20 minutes. Supernants were collected and kept at −20° C. IL-8 and TNF-α contained in the supernants were determined using an Enzyme linked immunosorbent assay kit. The amounts of IgG were determined by single immunodiffusion method. Briefly, rat sera were diluted and well mixed with 2% agar, which was pre-heated at 60° C. for several minutes. The sera-agar mixture was then solidified in a container. Loading wells were made in the solidified agar and diluted anti-IL-8 or anti-TNF-α antibodies were loaded into the wells. The solidified agar was then kept at 37° C. for 24 hours to allow formation of precipitate rings. The diameters of these rings were then determined. A standard curve was made and the concentration of serum IL-8 or TNF-α were then determined based on the standard curve.

All statistical analysis were performed using Student's t test. $p<0.05$ indicates that difference is significant.

All rats showed symptoms similar to that of inflammatory bowel diseases, for example, blooding, swollen, immune cell infiltration, and/or ulcer formation.

EXAMPLE 4

Effect of *Clostridium* and *Bacillus* on Inflammatory Bowel Disease in Rats

IBD was induced in 40 rats following the method described above. The 40 rat were divided into four groups (Groups A, B, C, and D) with 10 rats in each group. Group A was treated with physiological saline; Group B treated with mesalazine (200 mg/ml) at a dose of 1 ml/100 g body weight; Group C treated with *Clostridium butyricum* No. 0313.1 ($10^8$ CFU/ml) at a dose of 1 ml/100 g body weight; and Group D treated with *Bacillus coagulans* CGMCC No. 1207 ($10^8$ CFU/ml) at a dose of 1 ml/100 g body weight, for 21 days. During this period of time, the rats were weighed once every week. Their physical conditions and physical features of their feces were observed.

At day 21, the rats were sacrificed and the pathological condition of the rats' colonic walls were determined as described above.

a. Feces Features

Before treatment, all rats, in which inflammatory bowel diseases were induced, released whitish soft feces containing mucus. The feces features of the Group A rats kept the same during the 21-day treating period. Rats in other groups (B, C, and D), however, all released normal feces after the treating period.

b. Colon Wet Weight Index

Compared with Group A rats, which were treated with physiological saline, Group B rats (treated with mesalazine), Group C rats (treated with *B. coagulans*), and Group C rats (treated with *C. butyricum*) showed significantly reduced colon wet weight index ($p<0.05$). See Table 1 below.

TABLE 1

The Colon Wet Weight Index of Rats Having Inflammatory Bowel Diseases

| Group | Animal No. | Colon Wet Weight Index |
|---|---|---|
| Normal | 8 | 0.42 ± 0.04 |
| A (Control) | 10 | 0.44 ± 0.04 |
| B (mesalazine) | 10 | 0.38 ± 0.03* |
| C (*B. coagulans*) | 10 | 0.39 ± 0.06* |
| D (*C. butyricum*) | 10 | 0.39 ± 0.05* | t test, *p < 0.05 vs control group c. Mucous Membrane Ulcer Index

The mucous membrane ulcer indexes of Group B rats (mesalazine), Group C rats (*B. coagulans*), and Group D rats (*C. butyricum*) were significantly reduced after treatment compared to that of Group A rats (saline). The difference was statistically significant ($p<0.01$). The efficacy of the live bacteria (*B. coagulans* and *C. butyricum*) was better than that of mesazaline. See Table 2 below.

TABLE 2

Colonic Mucous Membrane Ulcer Index of Rats Having Inflammatory Bowel Disease

| Group | Animal No. | Mucous Membrane Ulcer Index |
|---|---|---|
| Normal | 8 | 0 |
| A (Control) | 10 | 28.7 ± 9.7 |
| B (mesalazine) | 10 | 15.4 ± 6.3* |
| C (*B. coagulans*) | 10 | 11.6 ± 8.4*^ |
| D (*C. butyricum*) | 10 | 8.1 ± 5.1*^ | t test: *p > 0.05 vs control;
^p < 0.01 vs control d. Mucous Membrane Damage Index

After treatment, the damage index of the rectum and lower part of the colon was smaller in Group B, C, and D rats than that in Group A rats, although the difference was not statistically significant. The damage index of the upper and middle parts of the colon, however, showed great difference between Group A rats and Groups B, C, D rats ($p<0.05$). See Table 3 below. Table 3. Mucous Membrane Damage Index of Rats Having Inflammatory Bowel Disease

TABLE 3

Mucous Membrane Damage Index of Rats Having Inflammatory Bowel Disease

| Group | Animal No. | Rectum, Lower Part of Colon | Upper and Middle Parts of Colon |
|---|---|---|---|
| Normal | 8 | 0 | 0 |
| A (Control) | 10 | 1.83 ± 1.17 | 3.2 ± 0.8 |
| B (mesalazine) | 10 | 2.17 ± 1.17 | 1.3 ± 1.3* |
| C (*B. coagulans*) | 10 | 1.17 ± 0.98 | 1.8 ± 0.8* |
| D (*C. butyricum*) | 10 | 1.50 ± 1.05 | 1.5 ± 1.1* | t test: *p < 0.05 vs control e. Mesentery Lymphocytes Stimulation Index

After IBD was induced in rats, their B lymphocytes stimulation index has increased. However, the differences of the stimulation index between induced rats and normal rats were not statistically significant. After treatment, the B cell stimulation indexes of Group B, C, and D rats were increased compared to control rats (Group A). The difference also had no statistical significance.

Different from the B cell stimulation index, the T cell stimulation index of induced rats was significantly decreased compared to that of normal rats ($p<0.05$). The T cell stimulation indexes of the treated rats (Groups B, C, and D) were significantly increased compared to that of control rats (Group A). See Table 4 below.

TABLE 4

Mesentery Lymphocytes Stimulating Index of Rat Having Inflammatory Bowel Disease

| | Stimulating Index (SI) | |
|---|---|---|
| Group | B Lymphocytes | T Lymphocytes |
| Normal | 1.15 ± 0.26 | 1.03 ± 0.20 |
| A (Control) | 1.24 ± 0.18 | 0.59 ± 0.20 |
| B (mesalazine) | 1.05 ± 0.22 | 1.53 ± 0.44* |
| C (*B. coagulans*) | 1.14 ± 0.19 | 1.25 ± 0.49* |
| D (*C. butyricum*) | 1.03 ± 0.29 | 1.73 ± 1.31* | t test: *p > 0.05 vs control f. Cytokines and IgG

The amounts of IL-8 and TNF-I in the sera of control rats (Group A) were much higher than those of the treated rats (Groups B, C, and D) ($p<0.05$). In rats treated with *B. coagulans* (Group C) or *C. butyricum* (Group D), the TNF-α levels were lower than those in rats treated with mesazaline (Group B). As to the levels of IgG, it was much higher in control rats (Group A) than in normal rats. Both *B. coagulans* and *C. butyricum* significantly decreased IgG levels in rats. Mesalazine slightly increases IgG levels; however, the increase was not statistically significant. The results are summarized in Table 5 below.

The rat IBD model is very close to human IBD. Results from this example showed that live beneficial bacteria, such as *B. coagulans* and *C. butyricum*, were effective in treating IBD. For example, these live bacteria reduced the areas of colonic mucous membrane ulcer and damage, colon wet weight, and levels of inflammation in colon and rectum. The treating efficacy of the live bacteria was better than Mesalazine, a drug commonly used for treating IBD.

TABLE 5

Cytokines and IgG in Rats Having Inflammatory Bowel Disease

| Group | IL-8 (pg/ml) | TNF-a (ng/ml) | IgG (mg/ml) |
|---|---|---|---|
| Normal | 37.3 ± 14.7 | 17.6 ± 5.0 | 7.5 ± 0.3 |
| A (Control) | 81.0 ± 10.9 | 57.4 ± 7.7^ | 11.9 ± 0.4^ |
| B (mesalazine) | 47.7 ± 16.9* | 66.6 ± 8.3 | 12.0 ± 1.8* |
| C (*B. coagulans*) | 39.7 ± 13.4* | 36.7 ± 15.0* | 9.6 ± 1.8* |
| D (*C. butyricum*) | 51.7 ± 13.0* | 38.3 ± 14.1 | 9.7 ± 2.1* | t test: ^p < 0.05 vs normal rats;
*p < 0.05 vs control rats

EXAMPLE 5

Effects of *C. butyricum* and *B. coagulans* in treating Crohn's disease

Ten patients (6 male, 4 female, average age 38) were diagnosed with Crohn's disease by clinical, colonscopic, histological, or barium x-rays examination. All of the patients had symptoms such as abdomen pain and diarrhea. These patients were randomly divided into two groups. One group was administered orally with *C. butyricum* capsules (420 mg per capsule, containing >$1.0 \times 10^6$ cfu/g), three capsules each time, 3-4 times per day, for 6-8 weeks. The other group was administered with *B. coagulans* tablets (350 mg per tablet, containing >$1.0 \times 10^6$ cfu/g), three tablets each time, 3-4 times per day, for 6-8 weeks. The patients were observed for clinical symptoms (e.g., abdomen pain and/or diarrhea) and colonic inflammation before and after treatment according to the standards set forth in the diagnostic and therapeutic suggestions revised By the Gastroenterology Branch of the Chinese Medical Association on the inflammatory bowel diseases in 2000. More specifically, Complete relief: disappearance of clinical symptoms and/or obvious amelioration of colonic inflammation based on colonscopic or barium x-rays examination.

Effective: amelioration of clinical symptoms and reduced levels of colonic inflammation.

Ineffective: no change of clinical symptoms and levels of colonic inflammation.

After treatment, all patients displayed various levels of amelioration of clinical symptoms and colonic inflammation. In the group of patients who took *C. butyricum* capsules, three showed disappearance of clinical symptoms, such as abdomen pain and diarrhea; two with ameliorated clinical symptoms and inflammation. Two patients taking *B. coagulans* tablets showed clinical alleviation of Crohn's disease and three showed effectiveness. No significant difference was observed in patients who took *C. butyricum* and in patients who took *B. coagulans* with respect to efficacy.

EXAMPLE 7

Effect of *C. butyricum* in Treating Ulcerative Colitis

Fifteen patients (9 male, 6 female, age 26-74, average age 48.4)) were diagnosed with ulcerative colitis by clinical, colonscopic, histological, or barium x-rays examination. These patients had a disease duration from 5 months to 20 years, average 4.7 years. One of the patients also had colonic polyp.

These patients were administered orally with *C. butyricum* capsules (420 mg per capsule, containing $>1.0\times10^6$ cfu/g), three capsules each time, 3-4 times per day, for 8 weeks. Their clinical symptoms, such as abdomen pain, diarrhea, abnormal feces features (e.g., loose, mucous, or blooding), and levels of colonic inflammation were observed before and after treatment according to the standards set forth in the diagnostic and therapeutic suggestions revised by the Gastroenterology Branch of the Chinese Medical Association on the inflammatory bowel diseases in 2000. More specifically, Complete relief: disappearance of clinical symptoms and normal colonic wall conditions based on colonscopic examination.

Effective: amelioration of clinical symptoms and reduced levels of colonic inflammation or pseudo-polyp formation based on colonscopic examination.

Ineffective: no change of clinical symptoms and levels of colonic inflammation.

Among the fifteen treated patients, ten were completely relieved from ulcerative colitis and five showed effectiveness. The overall effective rate of *C. butyricum* treatment for ulcerative colitis is 100%. See Table 6 below. No adverse side effects were observed during treatment.

TABLE 6

Effectiveness of *C. butyricum* in treating ulcerative colitis

| | Before Treatment (No. of Patient) | After Treatment (No. of Patient) |
|---|---|---|
| Abdomen pain | 8 | 1 |
| Diarrhea | 15 | 0 |
| Mucous or bloody feces | 9 | 0 |

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of treating an inflammatory bowel disease, comprising:

identifying a subject in need thereof, and administering to the subject a composition which contains an effective amount of *Clostridium butyricum* CGMCC No. 0313.1.

2. The method of claim 1, wherein the inflammatory bowel disease is Crohn's disease.

3. The method of claim 2, wherein the composition contains an effective amount of *Clostridium butyricum* CGMCC No. 0313.1.

4. The method of claim 3, wherein the composition contains $1\times10^6$ colony forming unit/g to $1\times10^{12}$ colony forming unit/g *Clostridium butyricum* CGMCC No. 0313.1.

5. The method of claim 1, wherein the composition contains an effective amount of *Clostridium butyricum* CGMCC No. 0313.1.

6. The method of claim 1, wherein the inflammatory bowel disease is ulcerative colitis.

7. The method of claim 6, wherein the composition contains an effective amount of *Clostridium butyricum* CGMCC No. 0313.1.

8. The method of claim 7, wherein the composition contains $1\times10^6$ colony forming unit/g to $1\times10^{12}$ colony forming unit/g *Clostridium butyricum* CGMCC No. 0313.1.

9. The method of claim 1, wherein the effective amount of *Clostridium butyricurn* CGMCC No. 0313.1 is within the range of $1\times10^6$ to $1\times10^{12}$ colony forming unit per day.

10. The method of claim 1, wherein the composition is administered orally.

11. The method of claim 1, wherein the composition is a pharmaceutical composition.

12. The method of claim 11, wherein the pharmaceutical composition is formulated in a form of tablet, capsule, powder, or liquid.

13. The method of claim 11, wherein the pharmaceutical composition contains $1\times10^6$ colony forming unit/g to $1\times10^{12}$ colony forming unit/g live beneficial bacteria.

14. The method of claim 1, wherein the composition is a food product or a food supplement.

* * * * *